United States Patent
Prinz et al.

(10) Patent No.: US 10,813,943 B2
(45) Date of Patent: Oct. 27, 2020

(54) THERAPEUTIC USE OF A STERILE AQUEOUS OPHTHALMIC SOLUTION

(71) Applicant: CROMA-PHARMA GESELLSCHAFT M.B.H., Leobendorf (AT)

(72) Inventors: Martin Prinz, Klosterneuburg (AT); Sonja Höller, Vienna (AT)

(73) Assignee: CROMA-PHARMA GESELLSCHAFT M.B.H., Leobendorf (AT)

( * ) Notice: Subject to any disclaimer, the term of this patent is extended or adjusted under 35 U.S.C. 154(b) by 0 days.

(21) Appl. No.: 15/769,477

(22) PCT Filed: Oct. 27, 2016

(86) PCT No.: PCT/EP2016/075938
§ 371 (c)(1),
(2) Date: Apr. 19, 2018

(87) PCT Pub. No.: WO2017/072235
PCT Pub. Date: May 4, 2017

(65) Prior Publication Data
US 2018/0296589 A1    Oct. 18, 2018

(30) Foreign Application Priority Data

Oct. 30, 2015 (EP) .................................... 15192361

(51) Int. Cl.
| | | |
|---|---|---|
| *A61K 31/722* | (2006.01) | |
| *A61K 9/00* | (2006.01) | |
| *A61K 9/08* | (2006.01) | |
| *A61P 27/04* | (2006.01) | |
| *A61K 47/02* | (2006.01) | |
| *A61K 47/12* | (2006.01) | |

(52) U.S. Cl.
CPC .......... *A61K 31/722* (2013.01); *A61K 9/0048* (2013.01); *A61K 9/08* (2013.01); *A61K 47/02* (2013.01); *A61K 47/12* (2013.01); *A61P 27/04* (2018.01)

(58) Field of Classification Search
CPC .......... A61K 31/722; A61K 9/00; A61K 9/08; A61P 27/04
See application file for complete search history.

(56) References Cited

U.S. PATENT DOCUMENTS 5,412,076 A    5/1995    Gagnieu

FOREIGN PATENT DOCUMENTS

| EP | 0 112 881 B1 | 4/1989 |
|---|---|---|
| EP | 1852106 | 11/2007 |
| WO | 2008/077172 A1 | 7/2008 |
| WO | 2008/094675 A2 | 8/2008 |
| WO | 2009/032526 A2 | 3/2009 |
| WO | 2009/132226 A1 | 10/2009 |
| WO | 2009/132227 A1 | 10/2009 |
| WO | 2009/132228 A1 | 10/2009 |
| WO | 2015/169728 A1 | 11/2015 |

OTHER PUBLICATIONS

American Optometric Association, 2019.*
Bastin et al., ACS Publications, Organic Process research and Development, Jul. 19, 2000.*
International Search Report dated Jan. 31, 2017, issued in PCT Application No. PCT/EP2016/075938, filed Oct. 27, 2018.
Written Opinion dated Jan. 31, 2017, issued in PCT Application No. PCT/EP2016/075938, filed Oct. 27, 2018.
Bonengel, Sonja, et al., "Thiomers—From bench to market", Journal of Controlled Release, Jun. 2014.
Garhofer, Gerhard, et al., "Chitosan-N-Acetylcysteine Eye Drops", 7th International Congress of Corneal Cross-Linking, Dec. 2011.
Hoeller, Sonja, et al., "Safety and Tolerability of Chitosan-n-acetylcysteine Eye Drops in healthy Young Volunteers", Investigative Ophthalmology & Visual Science Apr. 2011, vol. 52, 3841.
Hongyok, Teeravee, et al., "Effect of Chitosan-N-Acetylcysteine Conjugate in a Mouse Model of Botulinum Toxin B-Induced Dry Eye", Laboratory Sciences, Arch Ophthalmol 2009; 127(4): 525-532, Apr. 2009.
Jones, et al. "TFOS DEWS II—Management and Therapy", Tear Film & Ocular Surface Society Boston, MA, Downloaded Feb. 13, 2020.

* cited by examiner

*Primary Examiner* — Zohreh A Fay
(74) *Attorney, Agent, or Firm* — Workman Nydegger

(57) ABSTRACT

The present invention relates to a sterile aqueous ophthalmic solution comprising N-(N-acetylcysteinyl-)chitosan or a pharmaceutically acceptable salt thereof in a carrier solution, wherein the N-(N-acetylcysteinyl-)chitosan has a content of free thiol groups in an amount of from 80 μmol/g polymer to 280 μmol/g polymer, for the specific use in the prevention or treatment of dry eye syndrome or dry eye signs and/or symptoms wherein said solution is applied prior to sleep.

20 Claims, No Drawings

THERAPEUTIC USE OF A STERILE AQUEOUS OPHTHALMIC SOLUTION

The present invention relates to the therapeutic use of a sterile aqueous ophthalmic solution comprising N-(N-acetylcysteinyl-)chitosan or a pharmaceutically acceptable salt thereof in a carrier solution.

Dry eye syndrome (DES), also referred to as dry eye disease, is a highly prevalent ocular surface disease. Approximately 40 million Americans are affected with some type of dry eye, a significant portion of which that are age 50 years and older have moderate-to-severe dry eye (Schaumberg, Sullivan et al., 2003, Prevalence of dry eye syndrome among US women, Am J Ophthalmol (136): 318-326; Schaumberg, Dana et al., 2009, Prevalence of dry eye disease among US men: estimates from the Physicians' Health Studies, Arch Ophthalmol (127): 763-768).

Broadly, dry eye disease can be any syndrome associated with tear film instability and dysfunction (such as increased tear evaporation and/or reduced aqueous secretion). Among the indications that are referred to by the general term "dry eye disease" are: Keratoconjunctivitis sicca (KCS), age-related dry eye, Stevens-Johnson syndrome, Sjogren's syndrome (or Sjögren's syndrome), ocular cicatrical pemphigoid, corneal injury, ocular surface infection, Riley-Day syndrome, congenital alacrima, nutritional disorders or deficiencies (including vitamin deficiencies), pharmacologic side effects, glandular and tissue destruction, autoimmune and other immunodeficient disorders, and inability to blink in comatose patients. Also included are dry eye symptoms caused by environmental exposure to airborne particulates, smoke, smog, and excessively dry air; as well as contact lens intolerance and eye stress caused by computer work or computer gaming.

There are other diseases that have a high degree of co-morbidity with dry eye disease: Allergic conjunctivitis (seasonal and chronic), blepharitis and Meibomian gland dysfunction. These conditions affect the quality and stability of the tear film, which results in dry eye signs and symptoms.

Laser assisted vision correction procedures such as photorefractive keratectomy (PRK), laser-assisted sub-epithelial keratectomy (LASEK) and laser-assisted in situ keratomileusis (LASIK) also negatively influence tear film functionality and frequently cause (temporary) dry eye disease.

Currently the management of DES encompasses both pharmacologic and non-pharmacologic treatments, including environmental management, avoidance of exacerbating factors, lid hygiene, tear supplementation (artificial tears), secretagogues (to increase the production of tears), punctual plugs, anti-inflammatory agents (cyclosporine, steroids), moisture chamber, and even salivary gland auto transplantation (Behrens, Doyle et al., 2006, Dysfunctional tear syndrome: a Delphi approach to treatment recommendations, Cornea (25): 900-907). Currently available options for treating DES are inadequate. Even tear supplementation is not an ideal treatment option as it requires the subject to repeat artificial tear installation very many times during the day.

Various polymers have been disclosed as possible aids in providing some benefit to alleviating DES symptoms and in fact some artificial tears contain one or more polymers, including the currently top 5 best selling over-the-counter (OTC) products for dry eye within the EU (Celluvisc®, Systane®, Hylo-Comod®, Optive® and Artelac®). These polymers are intended to protect ocular mucous membranes and provide lubrication for the ocular surface. Examples include cellulose derivatives, hyaluronic acid, liquid polyols, polyvinyl alcohol, povidone, carbopol and hydroxypropyl-guar. Polymers used in products to treat DES have relatively short residence time on the ocular surface and require frequent instillation. In order to increase ocular residence time, some formulations contain petroleum jelly or mineral oil; however, due to significant blurring these highly viscous products can only be used in the evening prior to sleep. (Abelson et al., 2008, Tear Substitutes. In: Albert and Miller, eds. Principles and Practices of Ophthalmology, 3rd edition, vol. 1. Philadelphia: W. B. Saunders Company, 287-292). All other tear substitutes have to be instilled repeatedly during the day.

Some potential improvements to these polymers have been disclosed. One potential improvement could be to use a polymer that has significant mucoadhesive properties in order to increase residence time of the formulation on the ocular surface without causing significant blurring. Chitosan, a polycationic polymer which is derived from the natural polymer chitin, is well known for its mucoadhesive properties. Ocular residence time of ophthalmic formulations containing chitosan can be increased not only due to its viscosity enhancing properties but also because of interactions of chitosan with negatively charged mucins on the ocular surface (Wadhwa, Paliwal et al., 2009, Chitosan and its role in ocular therapeutics, Mini Rev Med Chem (9): 1639-1647). In addition, chitosan has antimicrobial activity against various pathogenic microorganisms (Felt, Carrel et al., 2000, Chitosan as tear substitute: a wetting agent endowed with antimicrobial efficacy, J Ocul Pharmacol Ther (16): 261-270; Dai, Tanaka et al., 2011, Chitosan preparations for wounds and burns: antimicrobial and wound-healing effects, Expert Rev Anti Infect Ther (9): 857-879).

Thiolation of polymers has been disclosed to further increase their mucoadhesive properties. EP 1126881 B1 discloses a mucoadhesive polymer comprising at least one non-terminal thiol group. The use of thiolated polysaccharides for preparing an implant for tissue augmentation is disclosed in WO 2008/077172, wherein said thiolated polymers are characterised by the formation of disulfide bonds which leads to a stabilisation of the polymeric network. The priority application of WO 2008/077172, A 2136/2006, discloses further application fields for thiolated polymers.

Modification of chitosan by covalent attachment of thiol group bearing ligands (i.e., thiolation) has been disclosed. It has also been disclosed that thiolation increases the mucoadhesive properties of chitosan (Kast and Bernkop-Schnurch, 2001, Thiolated polymers—thiomers: development and in vitro evaluation of chitosan-thioglycolic acid conjugates, Biomaterials (22): 2345-2352; Bernkop-Schnurch, Hornof et al., 2004, Thiolated chitosans, Eur J Pharm Biopharm (57): 9-17; Bernkop-Schnurch, 2005, Thiomers: a new generation of mucoadhesive polymers, Adv Drug Deliv Rev (57): 1569-1582; Schmitz, Grabovac et al., 2008, Synthesis and characterization of a chitosan-N-acetyl cysteine conjugate, Int J Pharm (347): 79-85). The antimicrobial efficacy of some thiolated chitosans was evaluated as well (WO2009132226 A1; WO2009132227 A1; WO2009132228 A1; Geisberger, Gyenge et al., 2013, Chitosan-thioglycolic acid as a versatile antimicrobial agent, Biomacromolecules (14): 1010-1017)

N-acetylcysteine (NAC) is a derivative of the thiol group bearing amino acid L-cysteine. NAC is a reducing agent with antioxidative activity. It is also well known for its ability to reduce mucus viscosity by reducing mucin disulfide bonds. Due to these mucolytic properties NAC is widely used to reduce mucus viscosity in broncho-pulmonary disorders with excessive mucus production. Topical ophthalmic formulations containing the mucolytic and antioxidant agent NAC are used for the treatment of corneal diseases such as meibomian gland dysfunction and DES (Lemp, 2008, Management of dry eye disease, Am J Manag Care (14): S88-101; Akyol-Salman, Azizi et al., 2010, Efficacy of topical N-acetylcysteine in the treatment of meibomian gland dysfunction, J Ocul Pharmacol Ther (26): 329-333). EP 0 551 848 B1 discloses an ophthalmic pharmaceutical composition for the treatment of DES containing NAC in a concentration between 3% and 5% (w/v) and polyvinylalcohol.

It has been disclosed that thiolation of chitosan using NAC increases its ocular residence time on rabbit eyes when compared with non-thiolated chitosan (Dangl, Hornof et al., 2009, In vivo Evaluation of Ocular Residence Time of $^{124}$I-labelled Thiolated Chitosan in Rabbits Using Micro-PET Technology, ARVO Meeting Abstracts (50): 3689).

It has been disclosed that N-(N-acetylcysteinyl-)chitosan HCl has some beneficial effect on the ocular surface of the mouse eye in mouse dry eye models (Hongyok, Chae et al., 2009, Effect of chitosan-N-acetylcysteine conjugate in a mouse model of botulinum toxin B-induced dry eye, Arch Ophthalmol (127): 525-532; Hornof, Goyal et al., 2009, Thiolated Chitosan for the Treatment of Dry Eye—Evaluation in Mice Using the Controlled-Environment Chamber Model, ARVO Meeting Abstracts (50): 3663).

Further publications reviewing and discussing various uses of thiolated polymers are listed below:

Hornof et al., Mucoadhesive ocular insert based on thiolated poly(acrylic acid): development and in vivo evaluation in humans; Journal of Controlled Release 89 (2003) 419-428; Hornof, M., In vitro and in vivo evaluation of novel polymeric excipients in the ophthalmic field, Thesis, University of Vienna, 2003; Bernkop-Schnurch et al., Permeation enhancing polymers in oral delivery of hydrophilic macromolecules: Thiomer/GSH systems, J. Contr. Release 93(2003) 95-103; M. Hornof et al., In Vitro Evaluation of the Permeation Enhancing Effect of Polycarbophil-Cystein Conjugates on the Cornea of Rabbits, J. Pharm. Sci. 91 (12) 2002, 2588-2592; and Clausen et al., The Role of Glutathione in the Permeation Enhancing Effect of Thiolated Polymers, Pharm. Res. 19 (5) 2002, 602-608; Yamashita et al., Synthesis and Evaluation of Thiol Polymers, J. Macromol. Sc. 26 (1989), 9, 1291-1304; Zheng et al., Disulfide Cross-Linked Hyaluronan Hydrogels, Biomacromolecules 3 (6) 2002, 1304-1311; Wang et al., Chitosan-NAC Nanoparticles as a Vehicle for Nasal Absorption Enhancement of Insulin, J. Biomed Mater Res Part B: Appl Biomater 88B: 150-161, 2009; WO 2008/094675 A2; U.S. Pat. No. 5,412, 076 A.

PCT/EP2015/059674 (not pre-published) discloses a sterile aqueous ophthalmic solution comprising about 0.05% to about 0.5% (w/w) of N-(N-acetylcysteinyl-)chitosan or a pharmaceutically acceptable salt thereof in a carrier solution, wherein the N-(N-acetylcysteinyl-)chitosan has a content of free thiol groups in an amount of from 80 µmol/g polymer to 280 µmol/g polymer, and the use of said solution for the treatment of dry eye syndrome. As standard for aqueous ocular lubricants, the aqueous ophthalmic solution is applied once or twice a day. Ocular lubricants are usually applied first thing in the morning when patients experience worsening of dry eye symptoms.

In some conditions the application of the aqueous ophthalmic solution comprising N-(N-acetylcysteinyl-)chitosan is associated with ocular side effects such as burning and stinging.

In other conditions the application of the aqueous ophthalmic solution comprising N-(N-acetylcysteinyl-)chitosan in the morning does not lead to an alleviation of dry eye symptoms such as burning, itching and stinging.

In consequence of experiencing a lack of improvement or even a worsening of their dry eye symptoms, some patients may interrupt or stop treatment with aqueous ophthalmic solution comprising N-(N-acetylcysteinyl-)chitosan leading to an ineffective treatment or prevention of dry eye syndrome or dry eye signs and/or symptoms.

It is an object of the present invention to provide a pharmaceutical preparation for specific use in prevention or treatment of dry eye syndrome or dry eye signs and/or symptoms with reduced undesired side effects and/or improved effect.

This object is solved by a sterile aqueous ophthalmic solution comprising N-(N-acetylcysteinyl-)chitosan or a pharmaceutically acceptable salt thereof in a carrier solution, wherein the N-(N-acetylcysteinyl-)chitosan has a content of free thiol groups in an amount of from 80 µmol/g polymer to 280 µmol/g polymer, for the specific use in the prevention of of dry eye syndrome or dry eye signs and/or symptoms wherein said solution is applied prior to sleep.

Preferred embodiments of the present invention are listed in the dependent claims.

DETAILED DESCRIPTION OF THE INVENTION

Surprisingly, an aqueous ophthalmic solution containing N-(N-acetylcysteinyl-)chitosan or a pharmaceutically acceptable salt thereof in a carrier solution is more effective in improving and or alleviating dry eye signs and/or symptoms when applied prior to sleep with the additional benefit of decreased ocular side effects such as burning and stinging than when applied in the morning or during the day.

In the following, the term "chitosan-NAC" stands for both N-(N-acetylcysteinyl-)chitosan and pharmaceutically acceptable salts thereof.

Without wishing to be bound by any theory, the beneficial effect of the application or administering of chitosan-NAC prior to sleep may be due to the formation of a protective layer supporting regeneration of corneal surface and limiting damage via inflammatory processes while sleeping.

The wording "prior to sleep" refers to an application before going to sleep. "Sleep" refers to a periodic physiological loss of consciousness. By "periodic" it is understood to mean a substantially uniform repeating pattern. For example, an adult may sleep approximately 8 hours per day. The application prior to sleep covers also the application at a time point prior to a period of night's rest or state of calm independent of loss of consciousness. With other words, the application is preferred before going to bed with the intention to sleep. Synonym terms could be "omne nocte on", a Latin term for "every night", or "hora somni", Latin for "at the hour of sleep". Thus, the application is preferred at bedtime.

In context of the present invention it is preferred that the medication is applied immediately before going to sleep. It is preferred that the wording used for instructing the application refers to going "to sleep" rather than going "to bed" as activities like reading or watching TV or the like should not be encouraged between application and the effective sleep.

Preferably, the ophthalmic solution for use according to the invention is applied 1 hour before to immediately prior to sleep, more preferably immediately prior to sleep.

The application of chitosan-NAC prior to sleep may be the only application per day. One significant advantage of the formulation used according to the present invention is that it has been found that, following a single instillation onto the subject's eye, chitosan-NAC has a restorative effect on the tear film thickness for up to 24 h. This means that a subject does not have to constantly instill the product in the eye as would be needed for tear replacement therapy, such as when using artificial tears. The daily topical dose of the aqueous ophthalmic chitosan-NAC solution, effective to reduce dry eye symptoms and/or to improve tear film composition can be divided among one or several unit dose administrations. A subject would use the product as needed, but generally this would not be more than twice a day and in many instances the product would be used only once a day. A preferred regimen for the chitosan-NAC solution of the present invention is one drop of 0.1% (w/w) solution per eye once a day. Thus, a significant advantage of the formulation of the present invention is that it could be a once a day product and would ensure better patient compliance.

The wording "once per day" for application of the composition for use according the invention is meant to be understood as one application per day, i.e. one time within 24 hours. The wording has a meaning equivalent to once daily, every day, the Latin expression "quaque die" and abbreviations q.d. (or qd) and o.d. (or od). If treatment or prevention is intended for both eyes, "once daily" refers to one application per eye.

Thus, in a preferred embodiment, the ophthalmic solution for use according to the present invention is applied once per day prior to sleep.

The method of the present invention is an improvement compared to the common treatment of dry eye syndrome with an ophthalmic solution comprising chitosan-NAC applied in the morning or during daytime, i.e. when being awake. The method is especially suitable for conditions associated with sensitive eyes where the application of an ophthalmic solution comprising chitosan-NAC may be accompanied with ocular burning and pain.

The present invention is suitable for treating any dry eye syndrome. Broadly, dry eye syndrome or dry eye disease as pertaining to the present invention can be any syndrome associated with tear film instability and/or dysfunction (such as increased tear evaporation and/or reduced aqueous secretion).

In a preferred embodiment the ophthalmic solution for use according to the present invention, the dry eye syndrome or dry eye signs and/or symptoms are related to chronic dry eye syndrome.

The term "chronic dry eye syndrome" refers to a condition wherein the dry eye symptoms are persistent or occurring regularly. According to the invention, a condition is considered chronic wherein a singular application of an ophthalmic solution comprising chitosan-NAC does not have a lasting effect on symptoms of the dry eye syndrome. Particular, the term "chronic dry eye syndrome" as understood according to the invention covers conditions wherein the application of an ophthalmic solution comprising chitosan-NAC applied in the morning or during daytime is not effective and/or associated with side effects that impact compliance in terms of adherence to daily application.

Particularly, the present invention is suitable for treating chronic forms of dry eye disease associated with pronounced dry eye symptoms, such as keratoconjunctivitis sicca (KCS), age-related dry eye, Stevens-Johnson syndrome, Sjogren's syndrome (or Sjögren's syndrome), ocular cicatrical pemphigoid, Riley-Day syndrome, congenital alacrima, nutritional disorders or deficiencies (including vitamin deficiencies), glandular and tissue destruction, autoimmune and other immunodeficient disorders, and lagophthalmos. Also included are dry eye symptoms caused by repeated environmental exposure to airborne particulates, smoke, smog, and excessively dry air; as well as chronic eye stress caused by daily computer work or computer gaming. Further included are dry eye syndromes occurring together with additional ocular diseases and/or conditions (e.g.blepharitis, meibomian gland disease, glaucoma), which require the daily application of multiple ocular medications.

After treatment by the present methods, one or more dry eye signs and/or symptoms are reduced or alleviated in the subject. Dry eye symptoms include dryness, burning, ocular itching, ocular discomfort, photophobia, foreign body sensation, blurry vision, grittiness, and visual disturbance and/or loss, including blurred vision, reduced reading speed, photophobia, and loss in visual acuity. Dry eye signs are assessed by measurements such as: corneal and/or conjunctival staining (using fluorescein, lissamine green or rose Bengal stain), Schirmer's strip testing, Zone-Quick threads, tear film osmolarity, tear break-up-time and tear meniscus height.

One reason the signs and/or symptoms of DES are improved using the formulation of the present invention is possibly the restorative effect of the formulation on the ocular tear film thickness, which may be caused by a chemical interaction of the thiolated chitosan with ocular surface mucins or the presence of a protective coating on the ocular surface which is formed by crosslinking of chitosan-NAC after application to the ocular surface, or a combination of both effects.

In order to achieve sustained reduction or alleviation of one or more dry eye signs and/or symptoms, the prevention or therapy may be continued for an application duration. It is believed that multiple applications on subsequent days may have beneficial effects over individual applications. The application duration may be 7 days or longer, alternatively the application duration may be 14 days or longer. It may be preferred that in case of chronic conditions associated with dry eye syndromes or signs the application period is extended. The application duration may be for example 28 days or longer.

In a preferred embodiment of the present invention the concentration of the N-(N-acetylcysteinyl-)chitosan or said pharmaceutically acceptable salt thereof in said ophthalmic solution is from 0.05 to 0.3% (w/w), preferably from 0.05 to 0.2% (w/w), more preferably 0.08-0.16% (w/w).

Furthermore, said pharmaceutically acceptable salt is preferably selected from the group consisting of salts of organic acids such as acetic, citric, formic and tartaric acid, and salts of mineral acids such as HCl and $H_2SO_4$.

The N-(N-acetylcysteinyl-)chitosan preferably has a content of free thiol groups in an amount of from 105 µmol/g polymer to 250 µmol/g polymer, preferably of from 110 µmol/g polymer to 250 µmol/g polymer, most preferably of from preferably 140 to 250 µmol/g polymer.

The amount of crosslinked thiol groups in the N-(N-acetylcysteinyl-)chitosan may be 30% or less of the total thiol groups therein, preferably 25% or less, most preferably 15% or less.

The amount of free thiol groups immobilised on chitosan-NAC in an aqueous ophthalmic solution can be determined by the skilled artisan in a known way, such as via Ellman's reagent.

In addition to the fact that a high amount of free thiol groups on the chitosan-NAC polymer in the aqueous ophthalmic solution is important, a low amount of crosslinked thiols (disulfides) on the chitosan-NAC polymer in the solution of the present invention is also preferable. During preparation and storage of the aqueous ophthalmic solution crosslinking of thiol groups immobilised on the chitosan-NAC can occur. A low amount of crosslinked thiols present in the formulation is a preferred parameter of the chitosan-NAC polymer formulation of the present invention.

Therefore, according to a preferred embodiment, the amount of crosslinked thiol groups in the N-(N-acetylcysteinyl-)chitosan is 30% or less of the total thiol groups therein, preferably 25% or less, most preferably 15% or less.

Especially, in this preferred embodiment, the amount of crosslinked thiol groups in the N-(N-acetylcysteinyl-)chitosan is 30% or less of the total thiol groups therein, preferably 25% or less, most preferably 20% or less after storage of the solution for at least 12 months at room temperature.

If the amount of crosslinked thiol groups present in the formula was too high, the properties of the aqueous ophthalmic solution could change outside of the desired parameters, for example, the viscosity of the aqueous ophthalmic solution could become too high to be suitable for eye drops.

As explained below in more detail, it has been found that it is possible to produce a chitosan-NAC the thiol groups of which are not or only minimally crosslinked, such as with an amount of crosslinked thiol groups of less than 5%, preferably 4% or less of the total thiol groups. Especially if such a chitosan-NAC is employed for the manufacture of the ophthalmic solution used according to the present invention, the free thiol groups tend to be stable during the entire life cycle of the solution:

Thus, it has been found that upon employing such a chitosan-NAC during production of the formulation the increase of crosslinked thiol groups is <10% of the amount of free thiol groups initially present on the chitosan-NAC raw material. Furthermore, during storage of the solution over 12 months or even 18 months the increase of crosslinked thiol groups is <15% of the amount of free thiol groups initially present in the formulation. Finally, even if a second container of the solution (as defined below) which provides an oxygen barrier is opened, 30 days after opening the increase of crosslinked thiol groups is <15% of the amount of free thiol groups initially present in the formulation before opening.

Essentially the thiolated chitosan ophthalmic formulation used according to the present invention is made according to the following steps:
1. Chitin is isolated from crustaceous shells, such as shrimp or snow crab shells,
2. Chitosan is prepared from chitin through a chemical process that is well known in the art as, for example alkaline deacetylation;
3. The chitosan is thiolated by the covalent attachment of a thiol bearing ligand, such as with the use of N-acetylcysteine as is set forth herein;
4. The chitosan-NAC is then formulated in the form of an aqueous ophthalmic solution as is set forth herein; and
5. The aqueous ophthalmic solution containing chitosan-NAC is then put into a suitable container that would ensure its stability as is set forth herein.

The chitosan-NAC used in the present invention needs to be water soluble in the concentration range useful for the preparation of the aqueous ophthalmic solution and the resulting solutions need to be clear and colorless. Salt formation of chitosan-NAC with organic or anorganic acids increases the aqueous solubility of chitosan. Suitable salts of thiolated chitosan of the present invention include any pharmaceutically acceptable salts with organic acids such as acetic, citric, formic and tartaric acid, as well as mineral acids such as HCl and $H_2SO_4$. The use of a chitosan-NAC hydrochloride salt is a preferred embodiment of the present invention.

What is important is that such reaction pathways and reaction conditions are used that after synthesis and purification essentially all thiol groups immobilised on the chitosan backbone are present in the free form and not in the crosslinked form as disulfides, i.e. are only minimally crosslinked. Virtually all attached thiols in the thiolated chitosan of the present invention are in the form of free thiol groups, i.e. they are not cross-linked. A minimal amount of crosslinking during synthesis is only acceptable as long as the viscosity of the thiolated chitosan remains within the stated parameters and its aqueous solubility is sufficient for the preparation of an aqueous ophthalmic solution.

It has been found that it is possible to manufacture chitosan-NAC with a very low or even zero degree of crosslinking of the thiol groups by exposing the chitosan-NAC to a reducing agent after its synthesis, for example after alkaline hydrolysis of the thioacetyl moieties. The reducing agent may be selected from the group of DTT, TCEP or $NaBH_4$, $NaBH_4$ being preferred. It has, furthermore, been found that the reduction step should be carried out at elevated temperature, such as 30° C. or more or preferably 40° C. or more. Furthermore, high amounts of reducing agents need to be employed, such as with a stoichiometric ratio of reducing agent to the chitosan backbone polymer of 2:1 or more.

Chitosan-NAC polymers with a degree of crosslinked thiol groups of less than 5%, preferably 4% or less of the total thiol groups can be synthesized according to this embodiment.

The viscosity in aqueous solution of the final chitosan-NAC used according to the present invention preferably falls within a certain range, and it was discovered that the viscosity of the chitosan-NAC only falls within this preferred range if during the production of the chitosan-NAC the chitosan-NAC is processed under certain conditions and within certain parameters, particularly according to the reduction conditions stated above, which lead to polymers which are only minimally crosslinked. The viscosity of the resulting product preferably falls within an acceptable range so that the chitosan-NAC will be most useful in the resulting eye drop formulation. Thus, the kinematic viscosity (0.5% in water at 25° C.) of the chitosan-NAC polymer is preferably within the range of about 1 to 15 mm2/s, more preferably within the range of about 2 to 10 mm2/s. If the viscosity is too high, then a useful eye drop solution cannot be made with the preferred concentration range of chitosan-NAC in the formulation, as the polymer will remain as an insoluble viscous mass in the container.

The chitosan-NAC needs to be purified to be useful in the formulation used according to the present invention (such as after step #3 above and, especially, after treatment of the chitosan-NAC with the reducing agent). The chitosan-NAC should be washed in such a way that the resulting product is pure. One known method is disclosed in Kast and Bernkop-Schnurch, 2001, Thiolated polymers—thiomers: development and in vitro evaluation of chitosan-thioglycolic acid conjugates, Biomaterials (22): 2345-2352.

Another method would be washing the chitosan-NAC with polar solvents followed by drying in order to remove the solvents. One preferred solvent is isopropyl alcohol, since it is non-toxic, readily available, and economical, however other solvents, and other alcohols other than isopropyl alcohol could work as well. This washing can be repeated as needed, depending upon the volume of solvent used each time. Preferably the washing and drying step is repeated at least one time.

The drying step can be conducted at room temperature and at standard humidity, but this process can be very time consuming. Therefore, the drying process is preferably conducted at an elevated temperature and/or under reduced pressure. The drying of the chitosan-NAC is preferably conducted at an elevated temperature of at least about 40° C. to about 70° C. and preferably for at least about five hours. A more preferred drying process is conducted at temperatures of at least about 50° C. to about 60° C. for about 10 to 24 hours. One preferred multi-step purification process would be to wash the chitosan-NAC polymer three times with isopropyl alcohol and to recover the solid by centrifugation followed by drying at about 60° C. for about 15 to 20 hours.

The aqueous ophthalmic solution used according to the present invention can contain at least one ophthalmic compatible excipient. Any excipient suitable for example to adjust the tonicity, the viscosity of the solution or to stabilise the pH, to increase the solubility of the active ingredient, to increase ocular comfort after application, or to stabilise the formulation in general, can be employed.

The pH of the aqueous ophthalmic solution is adjusted by adding any physiologically and ophthalmic acceptable pH adjusting acids, bases, or buffers to have a pH within the range of about 5.5 to about 7. A pH much below about 5.5 would be outside of the physiological acceptable parameters (the solution would cause a severe stinging or burning sensation in the eye). At a pH much above 7, forming a stable solution of the chitosan-NAC where it does not precipitate out of solution is difficult. Thus, due to the ease of formulating a stable solution, a pH below 7 is preferred. The preferred pH of the aqueous ophthalmic solution used according to the present invention is between about 5.8 to about 6.8, with a pH of 6.0 to 6.6 being most preferred.

Examples of suitable acids used in the formulation of the present invention include acetic, boric, citric, lactic, phosphoric, hydrochloric, and the like, and examples of bases include sodium hydroxide, sodium phosphate, sodium borate, sodium citrate, sodium acetate, sodium lactate, tromethamine, THAM (trishydroxymethylamino-methane), and the like. A preferred embodiment is a boric acid and sodium borate buffer system, which also contains a polyol such as mannitol to increase buffer capacity at the most preferred pH range of 6.0 to 6.6.

Examples of suitable excipients used in the formulation to increase stability of the formulation include disodium ethylenediaminetetraacetate ($Na_2$-EDTA), sodium metabisulfite, mannitol, polyethylene glycol and the like.

The osmolarity of the topical ophthalmic formulation used in the present invention is generally from about 150 to about 400 milliosmolar (mOsM), more preferably from about 200 to about 350 mOsM, with the osmolarity of about 250 to about 330 mOsM being most preferred. The osmolarity can be adjusted by using appropriate amounts of physiologically and ophthalmic acceptable ionic or non-ionic agents. Sodium chloride is a common osmotic agent. Equivalent amounts of one or more salts made up of cations such as potassium, ammonium and the like and anions such as chloride, citrate, ascorbate, borate, phosphate, bicarbonate, sulfate, thiosulfate, bisulfate, and the like can be used in addition to or instead of sodium chloride to achieve osmorality within the above-stated range. Further, non-ionic agents such as mannitol, dextrose, sorbitol, glycerol, glucose and the like can also be used to adjust the osmolarity. Sodium chloride and mannitol are the preferred agents to adjust osmotic pressure.

The ophthalmic formulation can contain lubricants to provide a high ocular comfort level suitable for the regular application necessary in the treatment of DES. There are many types of lubricating agents such as polyvinylpyrrolidone, polyvinylalcohol, liquid polyols, hyaluronic acid and pharmaceutically acceptable salts thereof, lubricin and cellulose derivatives; however preferred agents are polyethylene glycol and hydroxypropyl methylcellulose (HPMC).

In a preferred embodiment, the ophthalmic solution used according to the present invention contains the following excipients in addition to N-(N-acetylcysteinyl-)chitosan hydrochloride:

Boric acid in an amount from 1.0 to 16.0 mg/ml, preferably 8 to 16 mg/ml;

Polyethylenglycol 400 in an amount from 0.01 to 5.0 mg/ml, preferably 1 to 5 mg/ml;

$Na_2$-EDTA in an amount from 0.01 to 0.5 mg/ml;

Mannitol in an amount from 0.01 to 5.5 mg/ml, preferably 0.1 to 4 mg/ml;

Sodium chloride in an amount from 0.01 to 9 mg/ml, preferably 1 to 3 mg/ml; and

Hydroxypropyl methylcellulose in an amount from 0.01 to 20 mg/ml, preferably 1 to 3 mg/ml.

The ophthalmic solution used according to the present invention has to be sterile and can be sterilized in any suitable manner. One particular preferred sterilization method is sterile filtration. The ophthalmic solution according to the present invention can contain preservatives, such as benzalkonium chloride, although this is less preferred.

The aqueous ophthalmic solution containing chitosan-NAC can be administered to the eyes of a patient by any suitable means for topical administration. This is preferably in the form of an aqueous eye drop solution. This solution can be in a single use container that is sterile until opened and thus does not need to have a preservative, or it can be in the form of a multi-use container that remains sterile after opening or in a multi-use container with a formulation containing a preservative.

The thiol groups of chitosan-NAC polymers tend to form disulfide bonds in aqueous solutions, thus reducing the mucoadhesive properties of chitosan-NAC. It was discovered that this tendency depends on the presence of oxygen in the aqueous ophthalmic solution.

It has been found that it is possible to stabilize the free thiol groups of the chitosan-NAC employed according to the present invention in aqueous solution even more when storing the solution under oxygen-free conditions, or essentially oxygen-free conditions. The oxygen-free atmosphere can be a nitrogen atmosphere, vacuum atmosphere, or an atmosphere consisting of noble gases.

Thus, when the solution is put into a container it should be done so in the absence of oxygen. Further, after the container is filled with the aqueous ophthalmic solution of the present invention, it should remain oxygen free. Therefore, the present invention also contemplates the use of a container that keeps the aqueous ophthalmic solution free from oxygen during storage.

Accordingly, in the present invention preferably an essentially oxygen free container containing the aqueous ophthalmic solution is used. As "essentially oxygen free", an atmosphere with an amount of 1.5% oxygen or less is to be understood. The concentration of dissolved oxygen in solution during production of the formulation and filling into the containers is below 1.0 mg/L, more preferably below 0.5 mg/L, even more preferably in the range of 0.1 mg/L.

In a preferred embodiment, the container is made of a material that is impervious to oxygen such that after filling, the ophthalmic solution remains essentially oxygen free for an extended period of time. Such containers could be glass or glass lined polymers, metal or metal lined polymers. In another preferred embodiment, the container is made of a polymer that has contained therein an oxygen absorber that would prevent oxygen from entering the solution through the walls of the container. Such oxygen absorbers include iron salts, sulfites, ascorbic acid, unsaturated fatty acid salts, metal-polyamide complexes or palladium/$H_2$ based systems. For example, WO 09/32526 discloses a film having an active oxygen barrier layer comprising an oxygen scavenging composition blended of a thermoplastic resin having carbon-carbon double bonds substantially in its main chain, a transition metal salt, and an oxygen barrier polymer with oxygen barrier properties. Further, the container itself can be manufactured from a gas tight material with an oxygen scavenger embedded and an airless closure system.

In a preferred embodiment, there is provided a first container containing the ophthalmic solution and a second container containing said first container.

Thus, for example, the container that holds the ophthalmic solution of the present invention is itself contained inside of a gas tight sachet or pouch. In particular a sachet or pouch made of aluminium or an aluminium laminate or aluminium composition may contain therein one or more sub-containers (i.e. "first containers") containing the ophthalmic solution according to the invention. The second container, i.e. the sachet or pouch can also contain an additional oxygen absorber (for example PKT KH-20 Pharmakeep® or Stabilox® Oxygen Scavenger) as is used in some standard packaging. Even in the case where the sachet is sealed under vacuum or in an inert atmosphere, the addition of an oxygen absorber can be required in order to remove residual oxygen from the sub-container. The sachet can contain either one or more single dose containers or multi-dose containers, for example five single dose containers per sachet. In the case of the multi-dose container, it must preserve the ophthalmic solution according to the present invention in a sterile condition and in an essentially oxygen free condition.

The chitosan-NAC contained in the container preferably used according to the invention preferably has a content of free thiol groups of from 80 μmol/g polymer to 250 μmol/g polymer, preferably 105 μmol/g polymer to 250 μmol/g polymer after storage of at least 12 months at room temperature. This means that, the free thiol groups remain on the chitosan-NAC and that the resulting formulation is stabile over an extended period of time. This period of time is preferably at least about 12 months, more preferably at least 18 months, and even more preferably at least about 24 months. This long stability preference is due to the fact that some products end up having long storage times and delays in commercial delivery and supply chains that could result in a less stable product falling out of acceptable parameters.

Furthermore, preferably the amount of crosslinked thiol groups in the chitosan-NAC contained in the container is 30% or less of the total thiol groups therein, preferably 25% or less, most preferred 20% or less after being stored for at least 12 months, more preferably at least 18 months. As mentioned above, the stability of the free thiol groups in the solution is especially good if a chitosan-NAC with only a minimal degree of crosslinked thiol groups is employed for manufacturing the solution.

In the above-described embodiment where there is a second container, e.g. a gas tight sachet, containing one or more first container(s), e.g. single use containers made from LDPE, the content of free thiol groups in the solution preferably remains within the range as defined per the present invention after opening of the first container for at least 30 days. The therapeutic time needed for e.g. 5 containers is 5 days, thus this duration of stability is more than sufficient.

As mentioned above, it was found that especially if a chitosan-NAC with only a minimal degree of crosslinked thiol groups is employed for manufacturing the ophthalmic solution of the present invention, the free thiol groups remained stable even after the second container which provides the oxygen barrier was opened, i.e. it was found that 30 days after opening of the second container the increase of crosslinked thiol groups was <15% of the amount of thiol groups initially present in the solution before opening.

The present invention also relates to a method of treatment of dry eye syndrome or dry eye signs and/or symptoms, wherein an aqueous ophthalmic solution comprising N-(N-acetylcysteinyl-)chitosan as defined above is applied prior to sleep.

The present invention is concerned primarily with the treatment of human subjects, but can also be employed for the treatment of other mammalian subjects, such as dogs and cats, for veterinary purposes.

The invention is illustrated further by the following examples, which are not to be construed as limiting the invention to the specific procedures described therein.

EXAMPLES

Example 1

Case Study in Patients with Chronic and Severe Dry Eye Syndrome

A female patient diagnosed with Sjögren's syndrome and advanced glaucoma applied an aqueous ophthalmic solution with a pH of 6.3 comprising 0.1% w/w chitosan-NAC with a degree of modification of 210 μMol free thiol groups/g polymer, polyethylenglycol 40, hydroxypropyl methylcellulose and mannitol in a boric acid buffer once a day in the morning for 7 days in addition to four other prescribed ocular therapeutics (eye drops containing timolol and eye drops containing pilocarpine, ocular lubricants containing hypromellose and carbomer, respectively). After 7 days the patient stopped application because of severe ocular burning and pain.

A second female patient diagnosed with Sjögren's syndrome, rheumatism and polyneuropathy applied the same aqueous ophthalmic solution once a day in the morning for 14 days in addition to other ocular therapeutics (eye drops containing cyclosporine twice daily, ocular lubricants containing trehalose and sodium hyaluronate multiple times daily as needed). The patient reported ocular burning and stinging sensations and wanted to stop the treatment.

The patients were then advised to apply the aqueous ophthalmic solution once daily prior to sleep. Within 28 days dry eye signs (corneal staining) and symptoms improved in both patients. The best corrected visual acuity (BCVA) increased and stabilized. In addition both patients reported that additional lubricants had to be less frequently used.

The invention claimed is:

1. A method of treating dry eye syndrome, dry eye signs, and/or dry eye symptoms, comprising:
applying to an eye a sterile aqueous ophthalmic solution comprising N-(N-acetylcysteinyl-)chitosan or a pharmaceutically acceptable salt thereof in a carrier solution, wherein the N-(N-acetylcysteinyl-)chitosan has a content of free thiol groups in an amount of from 80 µmol/g polymer to 280 µmol/g polymer, and
wherein said ophthalmic solution is applied to the eye once per day prior to sleep and wherein said ophthalmic solution treats dry eye syndrome, dry eye signs, and/or dry eye symptoms.

2. The method according to claim 1, wherein said dry eye syndrome or dry eye signs and/or dry eye symptoms are related to chronic dry eye syndrome.

3. The method according to claim 1, wherein the concentration of the N-(N-acetylcysteinyl-)chitosan or said pharmaceutically acceptable salt thereof in said solution is from 0.05 to 0.3% (w/w).

4. The method according to claim 1, wherein said pharmaceutically acceptable salt is selected from the group consisting of salts of organic acids and salts of mineral acids.

5. The method according to claim 1, wherein the N-(N-acetylcysteinyl-)chitosan has a content of free thiol groups in an amount of from 105 µmol/g polymer to 250 µmol/g polymer.

6. The method according to claim 1, wherein the amount of crosslinked thiol groups in the N-(N-acetylcysteinyl-)chitosan is 30% or less of the total thiol groups therein.

7. The method according to claim 3, wherein the concentration of the N-(N-acetylcysteinyl-)chitosan or said pharmaceutically acceptable salt thereof in said solution is from 0.05 to 0.2% (w/w).

8. The method according to claim 3, wherein the concentration of the N-(N-acetylcysteinyl-)chitosan or said pharmaceutically acceptable salt thereof in said solution is from 0.08 to 0.16% (w/w).

9. The method according to claim 4, wherein said pharmaceutically acceptable salt is a salt of an organic acid selected from acetic acid, citric acid, formic acid, or tartaric acid.

10. The method according to claim 4, wherein said pharmaceutically acceptable salt is a salt of a mineral acid selected from HCl or $H_2SO_4$.

11. The method according to claim 5, wherein the N-(N-acetylcysteinyl-)chitosan has a content of free thiol groups in an amount of from 110 µmol/g polymer to 250 µmol/g polymer.

12. The method according to claim 5, wherein the N-(N-acetylcysteinyl-)chitosan has a content of free thiol groups in an amount of from 140 µmol/g polymer to 250 µmol/g polymer.

13. The method according to claim 6, wherein the amount of crosslinked thiol groups in the N-(N-acetylcysteinyl-)chitosan is 25% or less of the total thiol groups therein.

14. The method according to claim 6, wherein the amount of crosslinked thiol groups in the N-(N-acetylcysteinyl-)chitosan is 15% or less of the total thiol groups therein.

15. A method of treating dry eye syndrome, dry eye signs, and/or dry eye symptoms, comprising:
applying to an eye once per day prior to sleep in a subject in need thereof a sterile aqueous ophthalmic solution comprising N-(N-acetylcysteinyl-)chitosan or a pharmaceutically acceptable salt thereof in a carrier solution, wherein the N-(N-acetylcysteinyl-)chitosan has a content of free thiol groups in an amount of from 80 µmol/g polymer to 280 µmol/g polymer, and
wherein said ophthalmic solution treats dry eye syndrome, dry eye signs, and/or dry eye symptoms.

16. A method of treating chronic dry eye syndrome, comprising:
applying to an eye once per day prior to sleep in a subject in need thereof a sterile aqueous ophthalmic solution comprising N-(N-acetylcysteinyl-)chitosan or a pharmaceutically acceptable salt thereof in a carrier solution, wherein the N-(N-acetylcysteinyl-)chitosan has a content of free thiol groups in an amount of from 80 µmol/g polymer to 280 µmol/g polymer,
wherein the subject shows dry eye signs and/or symptoms, or
wherein the subject is repeatedly exposed to one or more of (i) environmental conditions selected from airborne particulates, smoke, smog, or excessively dry air, (ii) chronic eye stress caused by daily computer work or computer gaming, or (iii) daily application of multiple ocular medications due to additional ocular diseases and/or conditions selected from blepharitis, meibomian gland disease, or glaucoma, and
wherein said ophthalmic solution treats chronic dry eye syndrome.

17. A method of treating pronounced dry eye symptoms, comprising:
applying to an eye once per day prior to sleep in a subject in need thereof a sterile aqueous ophthalmic solution comprising N-(N-acetylcysteinyl-)chitosan or a pharmaceutically acceptable salt thereof in a carrier solution, wherein the N-(N-acetylcysteinyl-)chitosan has a content of free thiol groups in an amount of from 80 µmol/g polymer to 280 µmol/g polymer,
wherein the subject is diagnosed with a condition selected from the group consisting of keratoconjunctivitis sicca (KCS), age-related dry eye, Stevens-Johnson syndrome, Sjogren's syndrome, ocular cicatrical pemphigoid, Riley-Day syndrome, congenital alacrima, nutritional disorders or deficiencies including vitamin deficiencies, glandular and tissue destruction, autoimmune and other immunodeficient disorders, and lagophthalmos, or
wherein said ophthalmic solution treats pronounced dry eye symptoms.

18. The method according to claim 15, the N-(N-acetylcysteinyl-)chitosan or pharmaceutically acceptable salt thereof forming a protective layer supporting regeneration of corneal surface and limiting damage via inflammatory processes.

19. The method according to claim 16, the N-(N-acetylcysteinyl-)chitosan or pharmaceutically acceptable salt thereof forming a protective layer supporting regeneration of corneal surface and limiting damage via inflammatory processes.

20. The method according to claim 17, the N-(N-acetylcysteinyl-)chitosan or pharmaceutically acceptable salt thereof forming a protective layer supporting regeneration of corneal surface and limiting damage via inflammatory processes.

* * * * *

UNITED STATES PATENT AND TRADEMARK OFFICE
CERTIFICATE OF CORRECTION

PATENT NO. : 10,813,943 B2
APPLICATION NO. : 15/769477
DATED : October 27, 2020
INVENTOR(S) : Prinz et al.

It is certified that error appears in the above-identified patent and that said Letters Patent is hereby corrected as shown below:

In the Specification

Column 5
Line 35, remove "being"

Column 7
Line 24, change "chitosan-NAC the" to –chitosan-NAC, the–

Signed and Sealed this
Fifth Day of January, 2021

Andrei Iancu
*Director of the United States Patent and Trademark Office*